United States Patent

Hindley et al.

[11] Patent Number: 5,726,055
[45] Date of Patent: Mar. 10, 1998

[54] PROCESS FOR THE PREPARATION OF PHARMACEUTICALLY ACTIVE THIAZOLIDINE COMPOUNDS BY A YEAST REDUCTASE

[75] Inventors: Richard Mark Hindley, Epsom; Stefan Roland Woroniecki, Betchworth, both of England

[73] Assignee: SmithKline Beecham plc, Brentford, England

[21] Appl. No.: 244,263

[22] PCT Filed: Nov. 19, 1992

[86] PCT No.: PCT/GB92/02140

§ 371 Date: May 19, 1994

§ 102(e) Date: May 19, 1994

[87] PCT Pub. No.: WO93/10254

PCT Pub. Date: May 27, 1993

[30] Foreign Application Priority Data

Nov. 19, 1991 [GB] United Kingdom ............... 9124513

[51] Int. Cl.$^6$ .................................................. C12P 17/00
[52] U.S. Cl. .......................... 435/280; 435/117; 435/118; 435/119; 435/911
[58] Field of Search .............................. 435/117, 118, 435/119, 911, 280; 548/183, 227, 217; 546/275, 280; 544/73

[56] References Cited

U.S. PATENT DOCUMENTS

| | | | |
|---|---|---|---|
| 4,410,734 | 10/1983 | Martin | 568/715 |
| 5,002,953 | 3/1991 | Hindley | 514/275 |
| 5,232,925 | 8/1993 | Hindley | 514/272 |

FOREIGN PATENT DOCUMENTS

| | | |
|---|---|---|
| 0 008 203 | 2/1980 | European Pat. Off. . |
| 0 198 440 | 10/1986 | European Pat. Off. . |
| 207581 | 1/1987 | European Pat. Off. . |
| 0 306 228 | 3/1989 | European Pat. Off. . |
| 441605 | 8/1991 | European Pat. Off. . |

OTHER PUBLICATIONS

Chemical and Pharmaceutical bulletin, vol. 32, No. 9, 1984, Tokyo JP, pp. 4460–4465, Takashi Sohda et al.

Kieslida, K, "Microbial trans formations" 1976, Wiley and Sons, pp. 674–680.

ATCC Catalogue of Yeasts, 1990, pp. 50–53.

*Primary Examiner*—Irene Marx
*Attorney, Agent, or Firm*—Charles M. Kinzig; Edward T. Lentz; Stephen Venetianer

[57] ABSTRACT

A process for preparing 5-(4-[2-(N-methyl-N-(2-pyridyl) amino)-ethoxy]-benzyl)-2,4-thiazolidinedione, by treating 5-(4-[2-(N-methyl-N-(2-pyridyl)amino)-ethoxy] benzylidene)-2,4-thiazolidinedione with a free whole yeast cell culture or immobilized whole yeast cells from *Rhodotorula glutinis* CBS 4406 or *Rhodotorula rubra* CBS 6469 as the microbial reductase source and recovering 5-(4-[2-N-methyl-(N-(2-pyridyl)amino)ethoxy]-benzyl)-2,4-thiazolidinedione, or a salt thereof.

5 Claims, No Drawings

PROCESS FOR THE PREPARATION OF PHARMACEUTICALLY ACTIVE THIAZOLIDINE COMPOUNDS BY A YEAST REDUCTASE

This application was filed under 35 USC 371 as the national phase of PCT/GB92/02140.

This invention relates to a novel process for preparing certain substituted thiazolidinedione derivatives, to certain novel compounds, to pharmaceutical compositions comprising such compounds and to the use of such compounds in medicine.

European Patent Application, Publication Number 0 306228 discloses inter alia certain thiazolidinedione derivatives of formula (A):

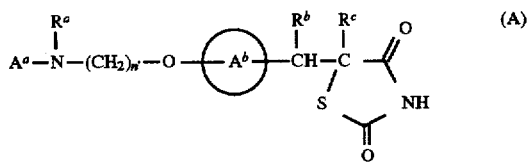

or a tautomeric form thereof and/or a pharmaceutically acceptable salt thereof, and/or a pharmaceutically acceptable solvate thereof, wherein: $A^a$ represents a substituted or unsubstituted aromatic heterocyclyl group;

$R^a$ represents a hydrogen atom, an alkyl group, an acyl group, an aralkyl group, wherein the aryl moiety may be substituted or unsubstituted, or a substituted or unsubstituted aryl group;

$R^b$ and $R^c$ each represent hydrogen or $R^b$ and $R^c$ together represent a bond;

$A^b$ represents a benzene ring having in total up to five substituents; and n' represents an integer in the range of from 2 to 6.

EP 0306228 also discloses a process for converting compounds of formula (A), in particular a process for reducing the benzylidene double bond of compounds of formula (A) wherein $R^b$ and $R^c$ together represent a bond to provide compounds of formula (A) wherein $R^b$ and $R^c$ each represent hydrogen.

Particular reduction methods disclosed in EP 0306228 are catalytic reduction methods and metal/solvent reducing methods.

It has now been discovered that the reduction of the benzylidene double bond of the compound of formula (A) may be effected by a reductase enzyme from a microorganism, in particular from a yeast microorganism, and surprisingly that the said reduction proceeds in a structure specific manner. The reduction is also capable of proceeding in an enantioselective manner.

Certain of the compounds obtained in the process are novel and are indicated to show good blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a process for preparing a compound of formula (I):

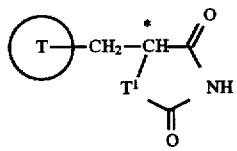

or a tautomeric form thereof and/or a pharmaceutically acceptable salt thereof and/or a pharmaceutically acceptable solvate thereof, wherein: T represents a substituted or unsubstituted aryl group and $T^1$ is O or S; which process comprises, treating a compound of formula (II):

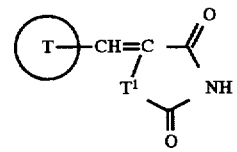

or a tautomeric form thereof and/or a salt thereof and/or a solvate thereof, wherein T and $T^1$ are as defined in relation to formula (I), with a microbial reductase obtained from an appropriate red yeast; and thereafter, as required, preparing a pharmaceutically acceptable salt and/or a pharmaceutically acceptable solvate of the compound of formula (I) or a tautomeric form thereof.

Suitably T represents a moiety selected from the list consisting of (Ia), (Ib), (Ic), (Id), (Ie), (If), (Ig), (Ih), (Ii), (Ij), (Il), (Im), (In), (Io) and (Ip):

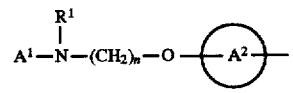

wherein $A^1$, $A^2$, $R^1$ and n are as defined in relation to formula (I) of EP 0306228;

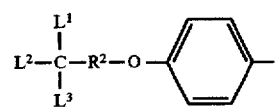

wherein $R^2$, $L^1$, $L^2$ and $L^3$ are as defined in relation to formula (I) of EP 0008203;

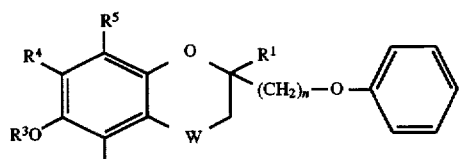

wherein $R^1$, $R^2$, $R^3$, $R^4$, $R^5$, W and n are as defined in relation to formula (I) of EP 0139421;

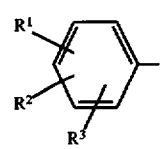

wherein $R^1$, $R^2$ and $R^3$ are as defined in relation to formula (I) of EP 0032128;

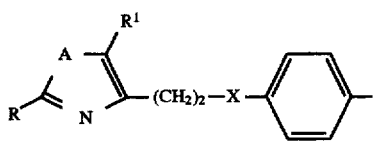

wherein A, R, R¹ and X are as defined in relation to formula (I) of EP 0428312;

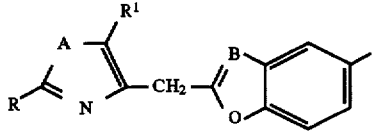

when A, B, R and R¹ are as defined in relation to formula (II) of EP 0428312;

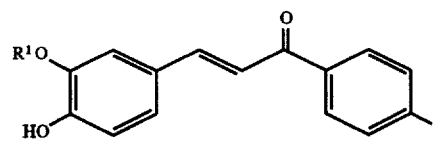

wherein R¹ is as defined in relation to formula (I) of EP 0489663;

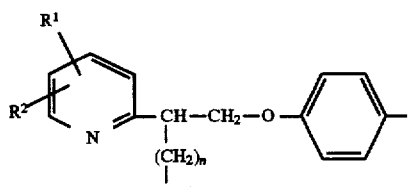

wherein R¹, R², R³ and n are as defined in relation to formula (I) of EP 0155845;

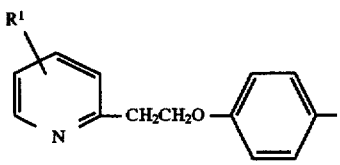

when R¹ is as defined in relation to formula (I) of EP 0257781;

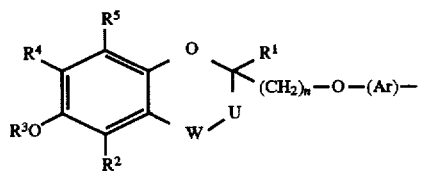

wherein Ar, R¹, R², R³, R⁴, R⁵, n, U and W are as defined in relation to formula (I) of U.S. Pat. No. 5,104,888;

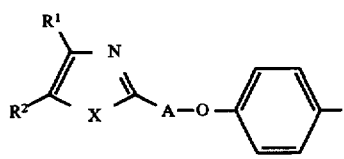

when A, R¹, R² and X are as defined in relation to formula (I) of EP 0208420;

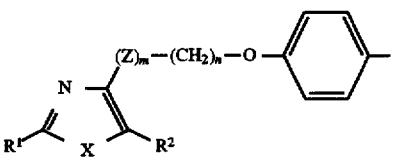

when R¹, R², X, Z m and n are as defined in relation to formula (I) of EP 0177353;

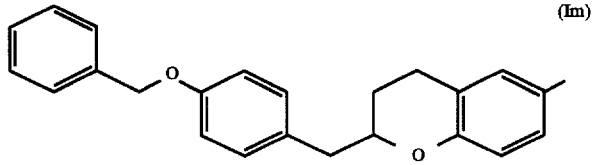

according to formula (I) of EP 0319189;

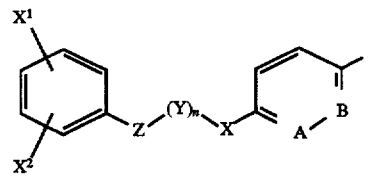

wherein A, B, X, X¹, X², n and Z are as defined in relation to formula (I) of EP 0332331;

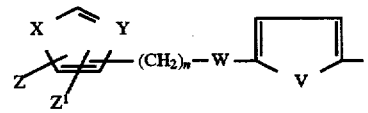

wherein V, W, X, Y, Z, Z¹ and n are as defined in EP 0332332; and

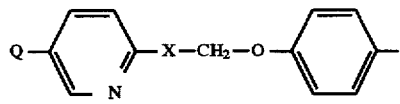

wherein Q and X are as defined in relation to formula (I) of International Application No. WO 92/18501.

Favourably, T represents a moiety of the above defined formula (Ia), (Ic), (Ie), (If), (Ii), (Ik) or (Io).

In particular T represents a moiety selected from the list consisting of (a), (b), (c), (d), (e), (f), (g), (h) and (i):

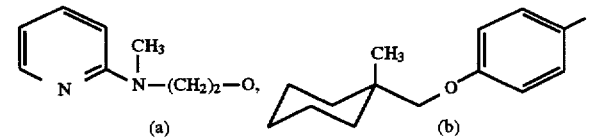

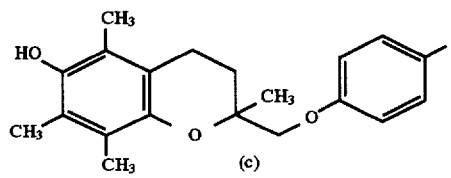

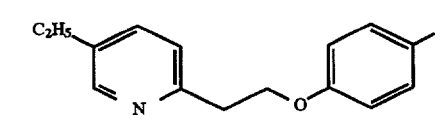

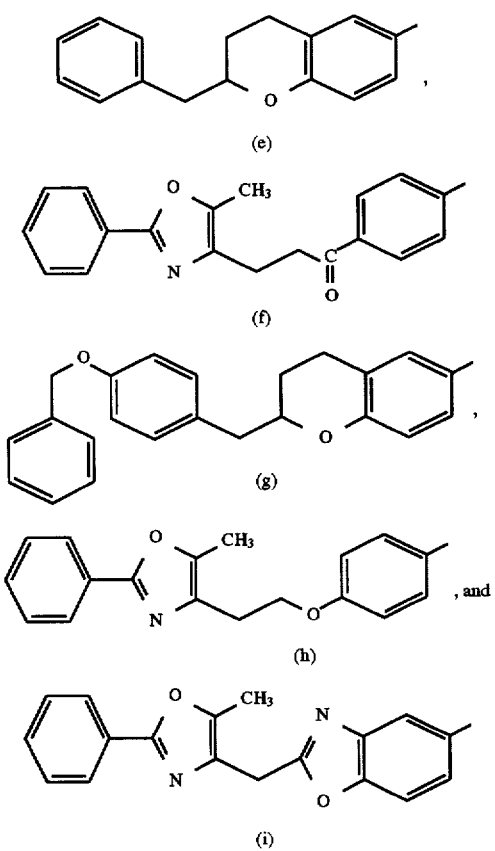

(e)

(f)

(g)

, and (h)

(i)

Suitably, T represents a moiety of formula (Ia) as defined above.

Preferably, T¹ represents S.

Thus, in a preferred aspect, the invention provides a process for preparing a compound of formula (I) as defined in EP 0306228: Accordingly, the invention provides a process for preparing a compound of formula (1):

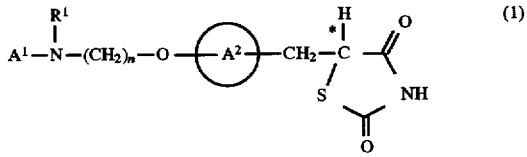

or a tautomeric form thereof and/or a pharmaceutically acceptable salt thereof, and/or a pharmaceutically acceptable solvate thereof, wherein:

A¹ represents a substituted or unsubstituted aromatic heterocyclyl group;

R¹ represents a hydrogen atom, an alkyl group, an acyl group, an aralkyl group, wherein the aryl moiety may be substituted or unsubstituted, or a substituted or unsubstituted aryl group;

A² represents a benzene ring having in total up to five substituents; and n represents an integer in the range of from 2 to 6;

which process comprises, treating a compound of formula (2):

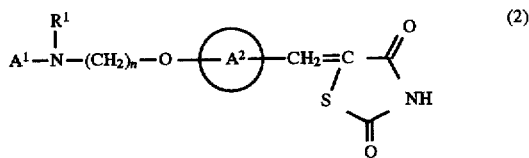

or a tautomeric form thereof and/or a salt thereof, and/or a solvate thereof, wherein A¹, A², R¹ and n are as defined in relation to formula (1) with a microbial reductase obtained from an appropriate red yeast; and thereafter, as required, preparing a pharmaceutically acceptable salt, and/or a pharmaceutically acceptable solvate of the compound of formula (1) or a tautomeric form thereof.

Unless mentioned to the contrary herein, the suitable, apt, favoured and preferred values for each variable in the above mentioned moieties of formula (Ia), (Ib), (Ic), (Id), (Ie), (If), (Ig), (Ih), (Ii), (Ij), (Il), (Im), (In), (Io) or (Ip) are as defined in the European and International patent applications or United States patents mentioned above in respect of each of the said formulae.

In particular, the suitable, apt, favoured and preferred values of the variables A¹, A², R¹ and n in formula (1) and formula (2) are as defined in relation to formula (I) of EP 0306228.

A most preferred value of A¹ in formula (1) and in formula (2) is a 2-pyridyl group.

A most preferred value of A² in formula (1) and in formula (2) is a moiety of formula:

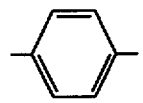

A most preferred value of R¹ in formula (1) and in formula (2) is a methyl group.

A most preferred value of n in formula (1) and in formula (2) is 2.

A most preferred value oft is a moiety of formula (a) as defined above.

A most preferred value of formula (1) is 5-(4-[2-(N-methyl-N-(2-pyridyl)amino)ethoxy]benzyl)-2,4-thiazolidinedione, or a tautomeric form thereof and/or a pharmaceutically acceptable salt thereof, and/or a pharmaceutically acceptable solvate thereof.

A most preferred value of formula (2) is 5-(4-[2-(N-methyl-N-(2-pyridyl)amino)ethoxy]benzylidene)-2,4-thiazolidinedione or a tautomeric form thereof and/or a salt thereof, and/or a solvate thereof.

Unless mentioned to the contrary herein, the suitable, apt, favoured and preferred pharmaceutically acceptable salts, pharmaceutically acceptable solvates and tautomeric forms of each of the compounds in the above mentioned moieties of formula (Ia), (Ib), (Ic), (Id), (Ie), (If), (Ig), (Ih), (Ii), (Ij), (Il), (Im), (In), (Io) or (Ip) are as defined in the European or International patent applications or United States patents mentioned above in respect of each of the said formulae.

In particular, suitable pharmaceutically acceptable salts include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

In particular, suitable pharmaceutically acceptable solvates include hydrates.

An appropriate red yeast is a red yeast which provides the above mentioned reduction, including known red yeasts and those red yeasts which may be produced from known red yeasts by conventional methods, such as conventional mutation methods, including the use of ultra-violet light, chemical mutagenic agents and genetic manipulation.

Particular red yeasts include those species of the genera Rhodotorula, Rhodosporidium or synonyms thereof.

Particular examples of the genera Rhodotorula include *Rhodotorula glutinis* CBS 4406, *Rhodotorula rubra* CBS 6469, *Rhodotorula rubra* CBS 17 and *Rhodotorula glutinis* IFO 0869.

Particular examples of the genera Rhodosporidium include *Rhodosporidium toruloides* CBS 14.

Suitable species of the genera Rhodotorula and Rhodosporidium and synonyms thereof are as disclosed in 'The Yeasts', 2nd edition, 1970, J. Lodder (ed.), North-Holland Publishing Co.

Known red yeasts may be obtained from the appropriate collection such as those disclosed in the National Collection of Yeast Cultures Catalogue, 1990, AFRC, Institute of Food Research, Norwich, UK

*Rhodotorula glutinis* CBS 4406, *Rhodotorula rubra* CBS 6469, *Rhodotorula rubra* CBS 17 and *Rhodosporidium toruloides* CBS 14 are known yeast microorganisms and may be obtained from Centraal bureau voor Schimmelcultures, Baarn, Delft, Netherlands. *Rhodotorula glutinis* IFO 0869 is a known yeast microorganism and may be obtained from the Institute for Fermentation, Osaka, Japan.

The compounds of formula (I) and formula (1) have at least one asymmetric carbon atom, indicated with an asterisk '*' in the formulae; they may therefore exist in at least two optically isomeric forms.

The compounds of formula (II) may be prepared according to known methods, for example by use of the appropriate method disclosed in the abovementioned European and International patent applications or U.S. patents. The contents of the abovementioned European and International patent applications and U.S. patents are incorporated herein by reference.

In particular compounds of formula (2) may be prepared according to the methods disclosed in EP 0306228.

The microbial reductase enzymes may be obtained from the appropriate red yeast by conventional culturing techniques such as those disclosed in J. Bacteriol., 1982, Vol. 150 498–505. H. Gilbert and M. Tully, European Patent Application No. 0198440 and British Patent No. 1,474,519.

The reductase may be isolated as a pure enzyme or, in the alternative a suitable source of the reductase may be incorporated into the reaction.

Suitable sources of the reductase include whole yeast cell cultures or immobilised yeast cells from the abovementioned organisms, suitably wherein the yeast cells are *Rhodotorula glutinis* CBS 4406 or *Rhodotorula rubra* CBS 6469.

The organisms may be grown in any suitable growth medium, including yeast extract, synthetic medium, for example peptone, or mixtures thereof, for example a yeast extract/peptone broth, at any temperature commensurate with growth of the organism, being generally an ambient or slightly elevated temperature, such as a temperature in the range of from 20° C. to 50° C. according to the nature of the organism employed, a suitable temperature being in the range of from 20° C. to 40° C., favourably, suitably 20° C. to 30° C., for example 28° C.

The reduction of the compound of formula (II) may be carried out in any suitable solvent, including the above mentioned growth medium, or, after separation and transfer of the cells or immobilised cells, in a salt solution, such as a buffer, for example an aqeous citrate buffer pH3.75 containing 5 w/v sucrose.

Generally, the compound of formula (II) is introduced into the reaction system as a solution in an organic solvent which may be a water miscible solvent such as dioxan, a partially miscible solvent, such as methyl acetate, or a water immiscible solvent, such as ethyl acetoacetate. The reaction may then carried out in the resulting single or two phase system.

The reaction may be carried out at any pH which provides a suitable rate of formation of the required product which is generally a pH in the range of from 2 to 10, such as in the range of from 2 to 7, 4 to 8 or 7 to 10, or more particularly in the range of from 2 to 4, 3 to 5, 4 to 6, 5 to 7, 6 to 8 or 8 to 10, for example at pH3 or pH8.

In one particular aspect of the invention, the reaction is carried out at an acidic pH, which is indicated to provide an stereoselective reduction of the substrate, to provide a product enriched in one enantiomer ('The selected enantiomer') of the asterisked carbon atom.

Accordingly, there is provided a process for the preparation of a compound of formula (I) (hereinafter referred to as the 'enantiomerically enriched compound (I)') wherein greater than 50% w/w of said compound is in the form of a compound of formula (IA):

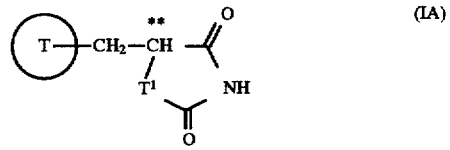

or a tautomeric form thereof and/or a pharmaceutically acceptable salt thereof and/or a pharmaceutically acceptable solvate thereof, wherein T and T¹ are as defined in relation to formula (I) and the '**' carbon atom is an enantiomeric carbon atom, which process comprises reacting a compound of the above defined formula (II) with a microbial reductase obtained from an appropriate red yeast and wherein the reaction is carried out at an acidic pH; and thereafter, as required, preparing a pharmaceutically acceptable salt and/or a pharmaceutically acceptable solvate of the enantiomerically enriched compound (I) or a tautomeric form thereof.

The values of variable T and T¹ in the compound of formula (IA) are as discussed above in respect of the compound of formula (I).

A most preferred form of the compound of formula (IA) is (+)5-(4-[2-(N-methyl-N-(2-pyridyl)amino)ethoxy]-benzyl)thiazolidine-2,4-dione, or a tautomeric form thereof and/or a pharmaceutically acceptable salt thereof and/or a pharmaceutically acceptable solvate thereof.

A suitable acidic pH is a pH in the range of from 2 to 6, especially 2 to 4, and preferably at pH3.

The stereoselective process provides the enantiomerically enriched compound (I) enriched in the enantiomer having the same stereochemistry at the asterisked carbon atom as the equivalent carbon atom in (+)-5-(4-[2-(N-methyl-N-(2-pyridyl)amino)ethoxy]-benzyl)thiazolidine-2,4-dione; X-ray analysis indicates this to be the (R)-enantiomer.

The reaction conditions, such as the particular acidic pH and the reaction temperature which provide optimum enrichment for any particular enantiomerically enriched compound (I) may be determined by routine experimentation.

Suitably, the stereoselective reaction provides enantiomerically enriched compound (I) wherein greater than 70% w/w is compound (IA); and favourably greater than 80% w/w. Most favourably, the product from the stereoselective process provides enantiomerically enriched compound (I) wherein 80–100% w/w is the compound of formula (IA), preferably 90–100%, such as 90–95%, and most preferably 95–100%, for example 95%, 96%, 97%, 98%, 99% or 100% w/w of compound of formula (IA).

The above mentioned enantiomerically enriched compound (I) is considered to form a further aspect of the present invention. Accordingly the present invention provides enantiomerically enriched compound (I) or a tautomeric form thereof and/or a pharmaceutically acceptable salt thereof and/or a pharmaceutically acceptable solvate thereof.

The present invention also provides enantiomerically enriched compound (I) or a tautomeric form thereof and/or a pharmaceutically acceptable salt thereof and/or a pharmaceutically acceptable solvate thereof, wherein greater than 50% w/w is in the form of compound (IA); suitably greater than 70% w/w and favourably greater than 80% w/w. Most favourably, the enantiomerically enriched compound (I) is in a form wherein 80–100% w/w is a compound of formula (IA), preferably 90–100%, such as 90–95%, and most preferably 95–100%, for example 95%, 96%, 97%, 98%, 99% or 100% w/w of a compound of formula (IA).

In one preferred aspect there is provided a compound of formula (IA) or a tautomeric form thereof and/or a pharmaceutically acceptable salt thereof and/or a pharmaceutically acceptable solvate thereof, preferably in optically pure form.

The absolute stereochemistry of compounds may be determined using conventional methods, such as X-ray crystallography.

The reductions may be carried out at any temperature which provides a suitable rate of formation of the required product, being generally an ambient or slightly elevated temperature, such as a temperature in the range of from 20° C. to 50° C., such as in the range of from 20° C. to 40° C. and preferably in the range of from 20° C. to 30° C., for example 28° C.

The product from any of the above reactions may be purified by phase separation and/or extraction into a suitable solvent, such as dichloromethane and thereafter, if required it may be chromatographed.

The above mentioned reactions may also be carried out using continuous production methods involving continuous recycling of the organic phase in the reaction or immobilisation of the cells and passing the substrate in organic solution over the immobilised biomass in a column, loop reactor or other similar reactor.

Immobilised cell preparations may be prepared according to conventional procedures, for example those disclosed in 'Alginate as immobilisation matrix for cells'; Smidsrod and Skjak-Braek, Tibtech 1990, 8, 71–78 or 'Immobilised enzymes and cells'; Rosevar, Kennedy and Cabral, IOP Publishing Ltd., 1987.

As mentioned above the enantiomerically enriched compound (I) is indicated as having useful therapeutic properties: The present invention accordingly provides enantiomerically enriched compound (I), or a tautomeric form thereof and/or a pharmaceutically acceptable salt thereof and/or a pharmaceutically acceptable solvate thereof, for use as an active therapeutic substance.

Thus the present invention provides enantiomerically enriched compound (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides enantiomerically enriched compound (I), or a tautomeric form thereof and/or a pharmaceutically acceptable salt thereof and/or a pharmaceutically acceptable solvate thereof, for use in the treatment and/or prophylaxis of hyperlipidaemia, hypertension, cardiovascular disease and certain eating disorders.

Enantiomerically enriched compound (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising enantiomerically enriched compound (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of enantiomerically enriched compound (I)), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of enantiomerically enriched compound (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the enantiomerically enriched compound (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of enantiomerically enriched compound (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of enantiomerically enriched compound (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Examples illustrate the invention. It will be appreciated that catalytic activity, and hence yields may be improved by carrying out strain improvement on the organism, by known techniques.

EXAMPLES: Preparation of Microbiological Culture Medium

The following microbiological culture media were used in the examples given:

Medium A; yeast extract (10 g), and mycological peptone (20 g) were dissolved in de-ionised water to make 1 liter and the pH was adjusted to 7.0–7.2 by the addition of 2M sodium hydroxide solution. This was dispensed in 90 ml volumes into 500 ml Erlenmeyer flasks prior to sterilisation, after which 10 ml of 30% w/v D-glucose solution was added to each flask with filter sterilisation.

Medium B; $(NH_4)_2HPO_4$ (13 g), $KH_2PO_4$ (7 g), yeast extract (3 g), $MgSO_4.7 H_2O$ (0.8 g), NaCl (0.1 g), $ZnSO_4.7 H_2O$ (60 mg), $FeSO_4.7 H_2O$ (90 mg), $CuSO_4.5 H_2O$ (5 mg) and $MnSO_4.4 H_2O$ (10 mg) were dissolved in de-ionised water to make 900 ml and the pH adjusted to 7.0–7.2 by the addition of 2M sodium hydroxide solution. This was dispensed in 90 ml aliquots into 500 ml Erlenmeyer flasks for pressure sterilisation after which 10 ml of 40% (w/v) D-glucose solution was filter sterilised into each flask.

Example 1: Reduction Using Free Yeast Cells

A loopful of *Rhodotorula rubra* CBS 6469 was used to inoculate a shake flask of medium A and this was incubated with shaking at 28° C. for 72 h. This broth (1 ml) was used to inoculate a similar flask of medium A which was shaken as before for 48 h prior to centrifugation. The pellet was resuspended in 0.1M Tris/HCl buffer pH8.0 containing 5% (w/v) sucrose giving a 1.3 relative broth coil density. To a portion of this suspension (40 ml) in a 250 ml Erlenmeyer flask was added 5-(4-[2-(N-methyl-N-(2-pyridyl)amino) ethoxy]benzylidene)thiazolidine-2,4-dione (7.5 ml of a 5 mg/ml solution in 1,4-dioxan) and the mixture shaken at 28° C. for 22 h. Centrifugation was followed by removal of 41.5 ml of supernatant which by hplc indicated an 80% production of 5-(4-[2-(N-methyl-N-(2-pyridyl)amino)ethoxy]-benzyl)thiazolidine-2,4-dione.

Example 2: Reduction Using Immobilised Yeast Cells

A loopful of *Rhodotorula rubra* CBS 6469 was used to inoculate a shake flask of medium B and this was incubated with shaking at 28° C. for 72 h. This broth (1 ml) was used to inoculate similar flasks of medium B which were shaken as before for 48 h prior to centrifugation of 120 ml of the broth. The resulting pellet was washed once in 0.1M Tris/HCl buffer pH8.0 and resuspended to 12.5 ml in this buffer. An equal volume of 2% (w/v) sodium alginate solution in the same buffer was added and the cells immobilised using standard methodology (Alginate as immobilisation matrix for cells. Smidsrod and Skjak-Braek, Tibtech 1990, 8, 71–78). The resulting beads were washed in the Tris buffer previously described and the volume made up to 40 ml with this buffer. To this suspension in a 250 ml Erlenmeyer flask was added 5-(4-[2-(N-methyl-N-(2-pyridyl)amino)-ethoxy] benzylidene)thiazolidine-2,4-dione (7.5 ml of a 5 mg/ml solution in 1,4-dioxan) and the mixture shaken at 28° C. for 22 h. The supernatant was decanted and the beads washed with 50 ml of 20% (v/v) 1,4-dioxan in the Tris buffer. Hplc of the combined solutions indicated a conversion to 87% of 5-(4-[2-(N-methyl-N-(2-pyridyl)amino)ethoxy]benzyl) thiazolidine-2,4-dione. The product was extracted into dichloromethane and the organic phase dried over magnesium sulphate and evaporated to yield the product as confirmed by spectroscopy.

Example 3: Reduction Using Free Yeast Cells

A loopful of *Rhodotorula rubra* CBS 6469 was used to inoculate a shake flask of medium A and this was incubated with shaking at 28° C. for 72 h. This broth (1 ml) was used to inoculate a similar flask of medium A which was shaken as before for 48 h prior to centrifugation of 10 ml of the broth. The pellet was resuspended in 0.3M Tris/HCl buffer pH8.0 containing 5% (w/v) sucrose to a volume of 4.0 ml. To this suspension in a 25 ml Erlenmeyer flask was added 5-(4-[2-(N-methyl-N-(2-pyridyl)amino)ethoxy] benzylidene)thiazolidine-2,4-dione (0.55 ml of a 8.33 mg/ml solution in 1,4-dioxan) and the mixture shaken at 28° C. for 4 h. Assay of the reaction mixture by hplc indicated a conversion to 59% to product (5-[4-(2-(N-methyl-N-(2-pyridyl)amino)ethoxy]-benzyl)thiazolidine-2,4-dione) which had an enantiomer ratio identical to a racemic standard.

Example 4: Production of Enantiomerically Enhanced Product

*Rhodotorula rubra* CBS 6469 was grown as described in Example 1, and the cell pellet from 66 ml centrifuged medium was resuspended to 25 ml in 0.1M citrate buffer containing 5% w/v sucrose at either pH 3.0, 3.5 or 4.0. To each was added 3.44 ml of a 8.33 mg/ml solution of 5-(4-[2-(N-methyl-N-(2-pyridyl)amino)-ethoxy] benzylidene)thiazolidine-2,4-dione in 1,4-dioxan. After shaking in flasks for 4 h the reaction mixtures were assayed by hplc for product.

| pH | % conversion to product | enantiomer ratio of product |
| --- | --- | --- |
| 3.0 | 71 | >98:<2 |
| 3.5 | 77 | 95:5 |
| 4.0 | 81 | 91:9 |

Using these results the pellet from 220 ml broth was resuspended in 88 ml of citrate buffer/sucrose pH 3.75 and to each of two 44 ml portions in 500 ml flasks was added 6 ml of the above substrate solution. After 3 h. 20 min shaking at 28° C. the reaction mixtures were centrifuged and the cells washed with 25 ml of 12%v/v 1,4-dioxan in the above buffer system. Hplc indicated a 94:6 enantiomer ratio of product in the combined supernatant.

The solution was reduced to ⅔rds original volume under vacuum at room temperature to remove dioxan. The solution was basified to pH8 using 10% aqueous ammonia and extracted with dichloromethane (3×50 ml). The combined organic extracts were dried ($MgSO_4$), filtered, evaporated to dryness under vacuum at <25° C. and the gummy product was dissolved in water (10 ml) containing concentrated hydrochloric acid (0.2 ml). After cooling to 2° C. for 24 hours this solid was filtered and dried under vacuum (20° C.) to give (+)-5-(4-[2-(N-methyl-N-(2-pyridyl)amino)ethoxy]-benzyl)thiazolidine-2,4-dione hydrochloride. (mp 123.5°–124° C.; water)

Example 5: Reduction using *Rhodotorula glutinis* CBS 4406

*Rhodotorula glutinis* CBS 4406 was cultured as described in Example 2, to provide 120 ml broth. The broth was centrifuged and resuspended to 12.5 ml in pH 8.0, 0.1M tris/HCl buffer containing 5% (w/v) sucrose. An equal volume of 2% (w/v) sodium alginate was added and the cells were immobilised as in Example 2, then resuspended to 40 ml in the above buffer. The suspension was dispensed into a 250 ml Erlenmeyer flask, to which was added 7.5 mls of a 5 mg/ml solution of 5-(4-[2-(N-methyl-N-(2-pyridyl)amino) ethoxy]benzylidene)thiazolidine-2,4-dione in 1,4-dioxan. The flask was shaken for 22 h at 28° C., then the supernatant was analysed using hplc which indicated a 51% production of 5-(4-[2-(N-methyl-N-(2-pyridyl)amino)ethoxy]benzyl) thiazolidine-2,4-dione.

Example 6: Reduction using *Rhodotorula rubra* CBS 6469

*Rhodotorula rubra* CBS 6469 was cultured as described in Example 1. Broth (12 mls) was centrifuged and resuspended to 4.0 ml in pH 9.0, 0.3M Tris/HCl buffer containing 5% (w/v) sucrose. The suspension was dispersed into a 25 ml Erlenmeyer flask, to which was added 0.55 ml of a 8.3 mg/ml solution of 5-(4-[2-N-(2-benzoxazolyl-(N-methyl) amino)ethoxy]benzylidene)thiazolidine-2,4-dione in 1,4-dioxan. The flask was shaken for 24 h. at 28° C., then the broth was analysed using hplc which indicated a 49% production of 5-(4-[2-N-](2-benzoxazolyl-(N-methyl) amino)ethoxy]benzyl)thiazolidine-2,4-dione.

We claim:

1. A process for preparing 5-(4-[2-(N-methyl-N-(2-pyridyl)amino)-ethoxy]-benzyl)-2,4-thiazolidinedione, which comprises, treating 5-(4-[2-(N-methyl-N-(2-pyridyl) amino)ethoxy]benzylidine)-2,4-thiazolidinedione with a free whole yeast cell culture or immobilized whole yeast cells from *Rhodotorula glutinis* CBS 4406 or *Rhodotorula rubra* CBS 6469 as the microbial reductase source and recovering 5-(4-[2-(N-methyl-N-(2-pyridyl)amino)ethoxy]-benzyl)-2,4-thiazolidinedione, or a salt thereof.

2. A process according to claim 1 on which the yeast strain is *Rhodotorula rubra* CBS 6469.

3. A process according to claim 2 wherein the reaction is carried out at an acidic pH.

4. A process according to claim 3 which is carried out at a pH of about 2 to 4.

5. A process according to claim 4 wherein the product is (+)-5-(4-[2-(N-methyl-N-(2-pyridyl)amino)ethoxy]-benzyl) thiazolidine-2,4-dione.

* * * * *